United States Patent [19]

Santa-Coloma Roth

[11] Patent Number: 5,034,215

[45] Date of Patent: Jul. 23, 1991

[54] CUTICLE AND NAIL CONDITIONING COMPOSITION

[76] Inventor: Nora Santa-Coloma Roth, 9205 Santayana Dr., Fairfax, Va. 22031-3067

[21] Appl. No.: 500,344

[22] Filed: Mar. 28, 1990

Related U.S. Application Data

[63] Continuation-in-part of Ser. No. 453,169, Dec. 26, 1989, which is a continuation of Ser. No. 251,819, Oct. 3, 1988, abandoned.

[51] Int. Cl.$^5$ ............................................... A61K 7/04
[52] U.S. Cl. ................................ 424/61; 424/195.1; 514/783; 514/785; 514/789
[58] Field of Search .............. 424/61, 195.1; 514/783, 514/789, 785

[56] References Cited

U.S. PATENT DOCUMENTS

| | | | |
|---|---|---|---|
| 3,628,974 | 12/1971 | Bettista | 424/73 X |
| 4,286,609 | 9/1981 | Miller | 132/75 |
| 4,530,828 | 7/1985 | Smith et al. | 424/70 X |
| 4,810,498 | 3/1989 | DiMeglio | 424/61 X |

*Primary Examiner*—Thurman Page
*Assistant Examiner*—Susan S. Rucker
*Attorney, Agent, or Firm*—Armstrong, Nikaido, Marmelstein, Kubovcik & Murray

[57] ABSTRACT

A composition for conditioning nails and nail cuticles, containing, in weight percent based on the total weight of the composition,
- (A) 53.0%–70.7% of anhydrous lanolin,
- (B) 12.0%–26.6% of peanut oil,
- (C) 2.9%–11.6% of olive oil,
- (D) 5.2%–16.4% of rose water, and
- (E) 0.9%–2.5% of vanilla extract.

3 Claims, No Drawings

CUTICLE AND NAIL CONDITIONING COMPOSITION

This application is a continuation-in-part of application Ser. No. 453,169, filed Dec. 26, 1989, which in turn is a continuation of application Ser. No. 251,819, filed Oct. 3, 1988, and now abandoned.

BACKGROUND OF THE INVENTION

This invention relates to a composition for personal body care and, more particularly, to a composition for conditioning cuticles and nails which is prepared from ingredients of natural, organic origin.

A number of compositions for conditioning or treating nails and nail cuticles are known. For example, Smith et al, U.S. Pat. No. 4,530,828, discloses a nail conditioning composition which is an aqueous emulsion of six essential active ingredients. Three of these active ingredients are in the aqueous phase: sodium lauryl sulfate, urea and hydrolyzed animal protein. The remaining three ingredients are in the oil phase: mineral oil, cholesterol and a lipid component. This composition has a high water content, with the ratio of the aqueous phase to the oil phase being in the range from 2:1 to 10:1 by weight. Additives which may be used in the composition include 0.5-5.0% w/w of emollients such as natural oils and lanolin derivatives (lanolin oil, lanolin wax, or lanolin alcohol).

Miller, U.S. Pat. No. 4,286,609, discloses a hot oil treatment composition which is a mixture of oils, emollients, emulsifiers, anti-oxidants, antibacterial agents, proteins and vitamins. The mixture is used by mixing it with hot water to give an emulsion in which the fingernails are soaked.

SUMMARY OF THE INVENTION

An object of this invention is to provide a composition for conditioning and moisturizing nails and nail cuticles. Another object is to provide a composition which prevents and cures hangnails. The composition of the invention is based on ingredients of natural origin and is hypoallergenic.

DESCRIPTION OF THE INVENTION

The composition of the invention comprises the following components in the following amounts, which are expressed in weight percent based on the total weight of the composition:

(A) anhydrous lanolin (53.0%–70.7%; preferably 58.0%–68.2%);
(B) peanut oil (12.0%–26.6%; preferably 15.0%–24.1%);
(C) olive oil (2.9%–11.6%; preferably 4.1%–8.7%);
(D) rose water (5.2%–16.4%; preferably 7.4%–14.3%); and
(E) vanilla extract (0.9%–2.5%; preferably 1.2%–2.2%).

Each of components (A)–(E) is readily available from commercial suppliers in grades suitable for use in compositions for personal body care.

The composition of the invention may be prepared by the following method. The peanut oil is first blended with the olive oil at room temperature, for example by using an electric mixer, and the resulting mixture is blended with the anhydrous lanolin until a mixture having a smooth texture is obtained. Then, the rose water and vanilla extract are blended with the resulting mixture until a completely homogeneous composition is obtained.

The following Example is described for the purpose of further illustrating the invention, without any intent of limiting the invention thereto.

EXAMPLE

Cuticle and Nail Conditioning Cream

A cuticle and nail conditioning cream was prepared by the above described method from the components shown in the following table, in which the proportions are percent by weight based on the total weight of the composition.

TABLE

| Component | Amount |
| --- | --- |
| anhydrous lanolin | 63.0% |
| peanut oil | 18.5% |
| olive oil | 6.1% |
| rose water | 10.7% |
| vanilla extract | 1.7% |

The obtained composition is a cream which restores flexibility and strength to damaged and brittle nails, softens and repairs damaged and dry cuticles, and heals the damaged skin around the nails. The conditioning cream of this example is also safe in that it contains no ingredient which would be harmful if ingested when the persons whose fingers are treated accidentally place them in their mouths.

This conditioning cream has a relatively simple formulation, as compared to conventional conditioning compositions for nails and cuticles which usually contain a much greater number of components. In particular, the conditioning cream of this example is hypoallergenic, and is free of the types of emulsifiers found in conventional nail conditioning compositions which may have an irritating effect on the skin of some consumers. The conditioning cream of this example surprisingly exhibits very little separation between the oily phase and the aqueous phase, even though it contains no emulsifiers.

The composition of this invention has a long shelf life, and is not a favorable medium for growth of bacteria or fungi, even though it contains no added synthetic preservatives or antibacterial agents.

The composition of the invention, however, may contain additives, such as waxes, gellants, emulsifiers, preservatives, emollients and fragrances, as long as the additives do not affect negatively the hypoallergenic, non-irritating characteristics of the composition.

I claim:

1. A composition for conditioning nails and nail cuticles, comprising:
   (A) 53.0%–70.7% of anhydrous lanolin,
   (B) 12.0%–26.6% of peanut oil,
   (C) 2.9%–11.6% of olive oil,
   (D) 5.2%–16.4% of rose water, and
   (E) 0.9%–2.5% of vanilla extract,
based on the total weight of the composition.

2. A composition as in claim 1, comprising:
   (A) 58.0%–68.2% of anhydrous lanolin,
   (B) 15.0%–24.1% of peanut oil,
   (C) 4.1%–8.7% of olive oil,
   (D) 7.4%–14.3% of rose water, and
   (E) 1.2%–2.2% of vanilla extract,
based on the total weight of the composition.

3. A composition as in claim 1, comprising:
   (A) 63.0% by weight of anhydrous lanolin;
   (B) 18.5% by weight of peanut oil;
   (C) 6.1% by weight of olive oil;
   (D) 10.7% by weight of rose water; and
   (E) 1.5% by weight of vanilla extract,
based on the total weight of the composition.

* * * * *